United States Patent [19]
Gesp

[11] Patent Number: 5,057,097
[45] Date of Patent: Oct. 15, 1991

[54] STRETCHABLE BUT STABLE FILM AND FASTENING TAPE

[75] Inventor: Marc Gesp, Turnhout, Belgium

[73] Assignee: Avery Dennison Corporation, Pasadena, Calif.

[21] Appl. No.: 243,917

[22] Filed: Sep. 13, 1988

[51] Int. Cl.$^5$ .............................................. A61F 13/15
[52] U.S. Cl. .................................... 604/389; 604/390; 428/43
[58] Field of Search ................. 604/389, 390, 374; 428/121, 41, 42, 43

[56] References Cited

U.S. PATENT DOCUMENTS

| | | | |
|---|---|---|---|
| 3,800,796 | 4/1974 | Jacob | 604/390 |
| 3,833,456 | 9/1974 | Reed et al. | 428/41 |
| 4,020,842 | 5/1977 | Richman et al. | 428/121 X |
| 4,051,853 | 10/1977 | Egan, Jr. | 604/390 |
| 4,066,081 | 1/1978 | Schaar | 604/390 |
| 4,111,205 | 9/1978 | Neimeth | 604/390 |
| 4,389,212 | 6/1983 | Tritsch | 604/389 |
| 4,643,729 | 2/1987 | Laplanche | 604/390 X |
| 4,795,456 | 1/1989 | Borgers et al. | 604/390 |
| 4,801,480 | 1/1989 | Panza et al. | 604/390 X |
| 4,813,947 | 3/1989 | Korpman | 604/390 X |

Primary Examiner—Richard J. Apley
Assistant Examiner—Rachel M. Healey
Attorney, Agent, or Firm—Pearne, Gordon, McCoy & Granger

[57] ABSTRACT

A web or film useful for fastener tapes for diapers consists of more than one layer and is characterized in that the outer layers, or at least one layer, are/is inelastic and the inner layer, or other layer, is elastic, and the film becomes substantially completely elastic, at least at one of its lengthwise portions, by manual stretching to cause yielding of the inelastic layer or layers.

13 Claims, 3 Drawing Sheets

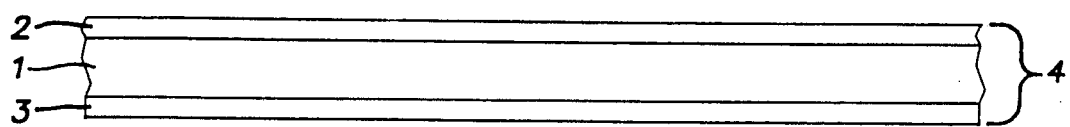
Fig.1
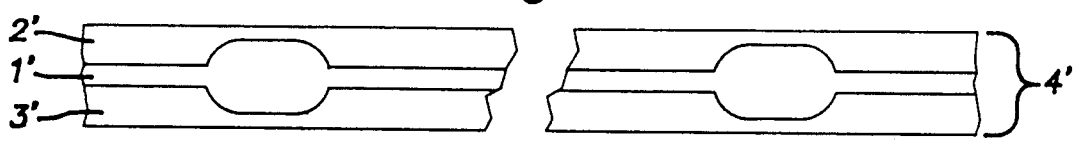
Fig.1A
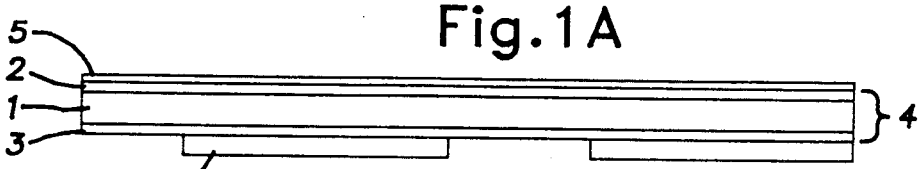
Fig.2
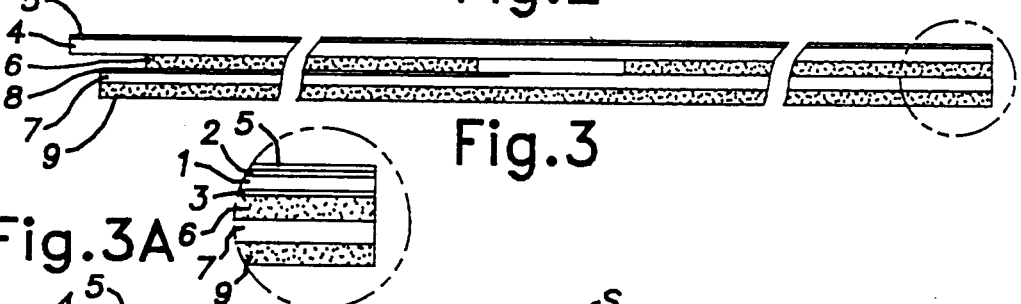
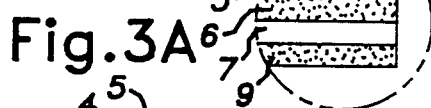
Fig.3
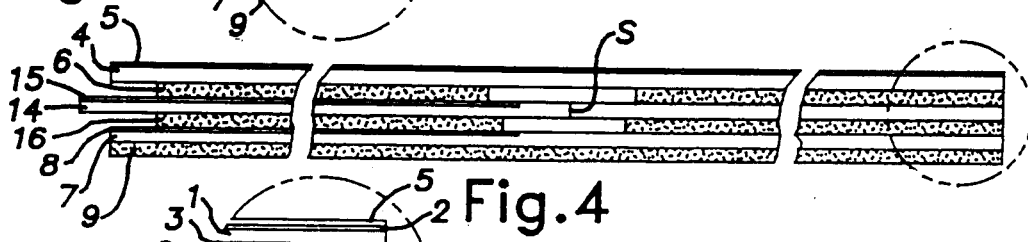
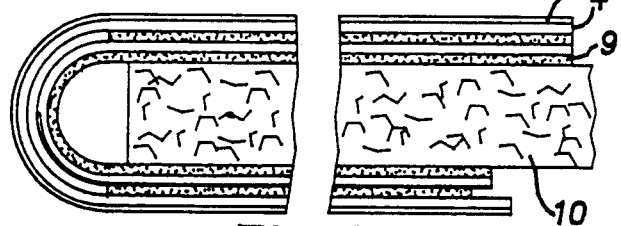
Fig.5
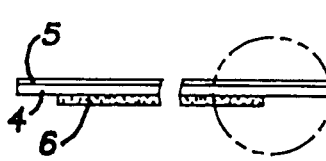
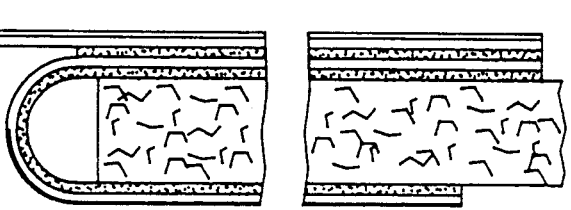
Fig.6A   Fig.6

STRETCHABLE BUT STABLE FILM AND FASTENING TAPE

This invention relates to a film consisting of multiple layers and to stretchable fastening tapes comprising said film.

BACKGROUND OF THE INVENTION

Stretchable fastening tapes which are suitable for disposable diapers or for other articles which are provided with a fastening tape, are already proposed previously as a means to improve the wear comfort of such articles. An initial proposal is described in U.S. Pat. No. 3,800,796. Improvements or alternatives thereof are e.g. described in U.S. Pat. No. 4,051,853 and U.S. Pat. No. 4,066,081. All stretchable fastening tapes known up to now comprise non-elastic and elastic portions which are applied in the lengthwise direction beside each other or partly on each other. Manufacturing such tapes is complicated, because various materials with exact dimensions have to be secured on each other or at each other. Another problem with stretchable fastening tapes is the need to avoid premature stretching of the fastening tape prior to fastening of the diaper, and in particular to stabilize the stretchable part of the fastening tape so as to allow accurate placement of tape on the diaper, which is not simple with a high line speed of manufacture.

SUMMARY OF THE INVENTION

Now a new film is developed consisting of more than one layer, characterized in that one or more layers are non-elastic and another layer is elastic, which film becomes substantially completely elastic by stretching beyond the yield strength of the non-elastic layer or layers.

The force required to stretch the film to achieve its elastic properties is proportional to the width or linear cross dimension of the film piece being stretched. Therefore, the film may be manufactured and processed in customary film sizes using conventional automated machinery which imposes insufficient forces to stretch the film. However, upon reducing the width dimension of the film in accordance with its final usage, the force required for stretching the film is also reduced and the elastic properties of the film may be readily achieved by manual stretching.

Such a film can be prepared in a conventional and simple manner, by e.g. co-extruding or laminating. As indicated, the film acts as an inelastic material prior to stretching and may have similar properties in both the machine direction and the machine cross-direction. Since the film exhibits its elastic properties only after stretching, these elastic properties give no problems when preparing, storing, transporting and converting the film.

Said layered film is particularly suitable for use as a stretchable fastening tape due to its properties. In tape applications, the bulk film and tape stock have an indeterminate length in the machine direction and a selected width, e.g. about 1.5 meters in the machine cross-direction. Upon conversion to tape products, the length of the tape extends in the cross-direction and the width of the tape extends in the machine direction.

In one embodiment the fastening tape according to the invention comprises the above mentioned layered film and a pressure-sensitive adhesive at least at the terminal segments in the lengthwise direction of one of the layers. By said terminal segments different parts of e.g. the disposable diaper can be fastened to each other.

Furthermore, the film according to the invention can be used in any known tab fastener, as e.g. in the "area divarification adhesive means" system of applicant's assignee (U.S. Pat. No. 3,833,456). Such embodiment of the invention comprises a tab fastener having length, width and thickness directions, comprising in the lengthwise direction terminal segments and a central segment between the terminal segments, and in the thickness direction an inner layer and an outer layer, the inner layer being permanently adhered to e.g. the diaper and the outer layer being permanently adhered to the inner layer at one of the terminal segments and releasably and reclosably adhered at the other terminal segment, the outer layer comprising the layered film according to the invention.

The fastening tape exhibits its elastic properties only after stretching when "putting on" the diaper. In principle the complete fastening tape may be elastic, but naturally only the part which is not secured with an adhesive to an inelastic surface contributes to the elasticity.

In the drawings, which are highly schematic, the thicknesses of the various layers are not to scale.

BRIEF DESCRIPTION OF THE DRAWINGS

FIG. 1 is a schematic cross-section in the machine cross-direction of a three layer film according to the invention.

FIG. 1A is a view similar to FIG. 1 illustrating another embodiment of a three layer film according to the invention.

FIG. 2 is a schematic cross-section in the lengthwise direction, on a somewhat smaller scale than FIG. 1, illustrating the use of the film shown in FIG. 1 as a principal component in a fastener tape.

FIG. 3 is a view similar to FIG. 2 illustrating the use of the film shown in FIG. 1 as a principal component in a diaper tap fastener.

FIG. 3A is a schematic enlargement of a portion of FIG. 3.

FIG. 4 is a view similar to FIG. 3 but illustrating the use of the film of FIG. 1 as a principal component in another diaper tab fastener.

FIG. 4A is a schematic enlargement of a portion of FIG. 4.

FIG. 5 is a view similar to FIG. 3 showing the diaper tab fastener of FIG. 3 mounted on a diaper.

FIG. 6 is a view similar to FIG. 5 showing the mounted diaper tab fastener deployed for use as a fastener.

FIG. 6A is a schematic enlargement of a portion of FIG. 6.

DETAILED DESCRIPTION OF THE INVENTION

Figure 7:
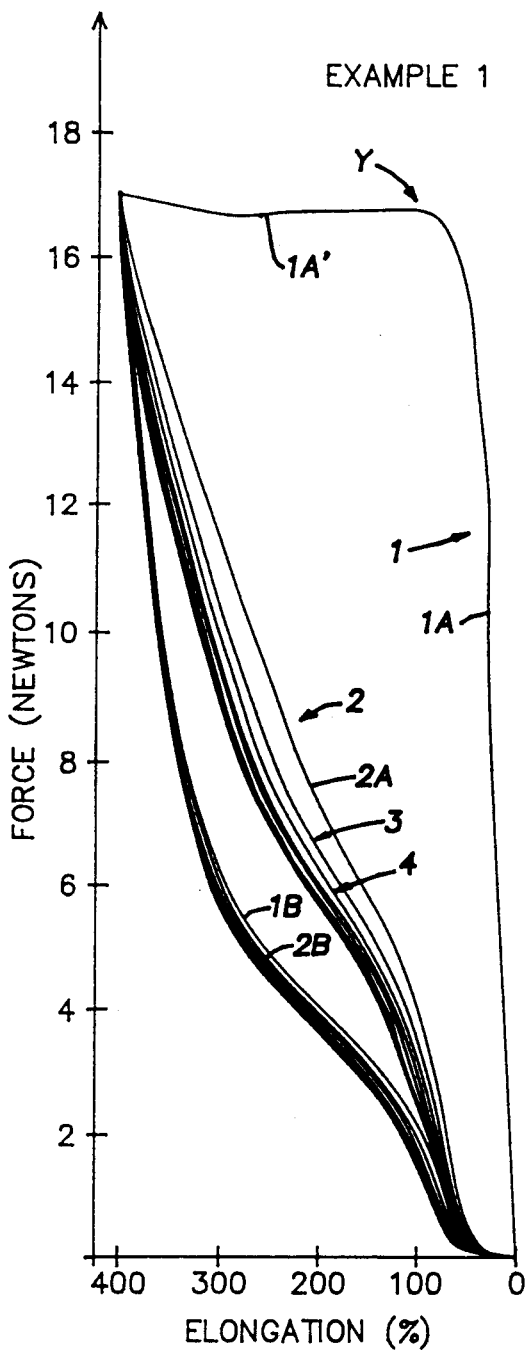
FIG. 7 is a reproduction of stress-strain curves for multiple sequential elongation and recovery cycles for the film of Example 1.

A three layer film according to the invention is shown in FIG. 1. This film 4 comprises a middle layer 1 of elastic material and outer layers 2 and 3 of non-elastic material. The elastic material may be elastic banding or woven elastic thread, and may be made from any elastomer, such as rubber, polyurethane, butadiene-styrene block polymer and a blend of different elastomers or blends of elastomers with plastics such that the blend retains its elastomeric properties. Good results are e.g. attained with a blend of SBS block copolymer sold under the trademark KRATON 1102 by Shell Chemical Company and low density polyethylene in weight ratios of 80:20 to 90:10. The elastic materials may in principal be any such materials. The outer layers 2 and 3 are inelastic and may each be of a different material than the other. The middle layer 1 and the outer layers 2 and 3 have to be capable of forming a good bond, heat assistance of the bond formation being utilized if required. Examples of suitable materials are polypropylene, polyvinylchloride, high density polyethylene, low density polyethylene, paper, non-woven fiber web etc.

The thicknesses of the layers are not very critical and are in general for the middle layer 1, 5–500 microns (0.2–20 mils), and for the outer layers 2 and 3, 5–200 microns (0.2–8 mils). In a typical example of a suitable film, layer 1 has a thickness of 100–200 microns (4–8 mils), and the outer layers 2 and 3 each have a thickness of 10–40 microns (0.4–1.6 mils). As the thicknesses of the outer layers are increased, higher forces are required in order to obtain elasticity.

Referring to FIG. 2, a simple form of fastener tape embodying the invention comprises the film 4 of FIG. 1 having a release 5 such as a coating of silicone applied to outer layer 2 and an adhesive layer such as a pressure-sensitive adhesive layer 6 applied to the terminal segments of the outer layer 3. The adhesive layer may be of different adhesives at each terminal segment, e.g. a pressure-sensitive adhesive may be used at the left terminal segment and a heat activated adhesive at the right terminal segment of the fastener tape as shown in FIG. 2. The interruption of the adhesive layer 6 tends to accommodate stretching of the film 4 to achieve its elastic properties at a selected intermediate location.

The inclusion of a second outer layer, e.g. outer layer 3 in FIG. 2 and the application of the pressure-sensitive adhesive thereto may be desirable especially in connection with adhesives having undesirable high migration characteristics. In such cases, the layer 3 may also serve as a barrier to tackifier migration from the adhesive to layer 1, thereby avoiding deterioration of the adhesive due to loss of tackifier.

As shown in FIG. 2, the release 5 is provided to allow pressure-sensitive tape stock embodying the invention to be stored and transported in bulk roll form. Similar provision for self-winding of pressure-sensitive adhesive tape stocks is well-known practice in the art. Release coatings of silicone and the like are commercially available in great variety.

The construction shown in FIG. 2 is dimensionally stable because the inelastic layers 2 and 3 stabilize the layer 1 and the remainder of the construction. The construction remains stable throughout the manufacturing process and may be processed with automatic film handling and processing machinery which imposes forces in both the machine and cross directions, the latter generally comprising vector components of the former. Accordingly, fastener is rendered elastic by the end user, as described below.

FIG. 3 schematically shows a diaper tab fastener construction of the "Y-configuration" type using the film 4 of FIG. 1. On the top side of the film 4 is applied a release 5 such as a coating of silicone. At the bottom side an adhesive layer 6 is applied at the terminal segments, with a gap at the central segment being positioned at any desired intermediate location. The layers 4, 5 and 6 together form the outer layer of the tab fastener. The release 5 is provided for storage and transport in bulk roll form and for self-winding.

The inner layer of the tab fastener consists of a layer 7, a release layer 8 such as a coating of silicone, and an adhesive layer 9. The layer 7 is formed of plastic such as polyester, polypropylene or high density polyethylene or paper such as Belgian glassine, 40 grade white. The release layer 8 extends along only one terminal segment of the diaper, as shown, thereby employing in the fastener construction the "area divarication" principle taught in U.S. Pat. No. 3,833,456 of common assignee, above-mentioned, whose disclosure is adopted by reference.

The pressure sensitive adhesives which may be used in the diaper tab fastener of FIG. 3, are known as such for similar articles. They should have a good tack, good cohesion strength, good urine resistance and good resistance to aging and should cause no skin irritation or disease. Most of such pressure sensitive adhesives are rubber-based adhesive, but acrylic or other pressure-sensitive adhesives may be utilized.

As schematically shown in FIG. 5, the stabilized diaper tab fastener of FIG. 3 is adhered at a side of the diaper by means of layer 9. This is a step in manufacture of diapers employing the fastening system construction. The interface between the adhesive layer 9 and a diaper to which the tab fastener is applied at the factory is sometimes referred to in the art as the "factory joint." Sometimes a diaper manufacturer may prefer to form the bond at the factory joint by use of an adhesive other than a pressure sensitive adhesive, such as a heat activated adhesive or a "room-temperature non-tacky" adhesive that is rendered tacky at elevated temperatures. Accordingly, the layer 9 may comprise any of these adhesives known to the art.

When the diaper is being put on an infant or incontinent adult, the bond between the layer 6 and release 8 is broken by manually lifting the associated terminal segment of the outer layer of the tab fastener so that it is deployed as shown in FIG. 6 for application on another part of the diaper. At the same time, the central segment of the outer layer between the two terminal segments is also deployed as seen in FIG. 6. As the deployed terminal segment of the outer layer, along with the central segment, is manually pulled to be thereby stretched around the body of the infant or adult to whom the diaper is being applied, a given tension or range of tensions is reached corresponding to the mechanical yield point or range of the material of layers 2 and 3 and therefore sufficient to overcome the dimensional stability of the layers 2 and 3 and cause them to inelastically yield. Such yielding tends to occur preferably or entirely at the central segment. However, layer 1 remains elastic throughout its length at all times. The diaper is now fastened around the body of the baby or adult to give a comfortable fit, and due to the elasticity present, the diaper can move along with all movements of the baby or adult while continuing to fit comfortably.

Yielding of the layers 2 and 3 may be accompanied by or evidenced by visible evidence of mechanical failure of the material comprising layers 2 and 3, such as visible wrinkles, striations or cracks as indicated schematically by small "x's" in FIG. 6A. It is believed that thereafter the failed portions of films 2 and 3 perform no structural function, and are merely carried as collections of discrete or semi-discrete pieces of film on layer 1 to which they remain bonded by the bond established by, for example, coextrusion.

The disposition of the release 5 over such portion of the layer 2 may be indeterminate after the layer 2 has yielded under tension, but since release 5 has already served its purpose (having allowed self-winding of the bulk stock for manufacture and storage prior to manufacture of individual diaper tab fasteners from such stock), such indeterminacy is of no consequence.

The tendency of the layers 2 and 3 to yield at the central segment may be enhanced by reducing the thickness of these layers adjacent the central segment. As shown in FIG. 1A for example, film 4' includes a middle layer 1' having a plurality of central segment portions of increased thickness and outer layers 2' and 3' having central segment portions of reduced thicknesses at spaced locations along the machine cross-direction of the film. (It should be appreciated that the tape products herein are produced in multiple lengths in the machine cross-direction of the bulk film and tape stock.) Upon use of the film 4' in the diaper tab of FIG. 3, the central segment portions of the layers 1', 2' and 3' are positioned in a lengthwise direction in substantial alignment with the gap at the central segment of the adhesive layer 6. Such thickness variations also enable the mechanical yield point or range, where the layers 2' and 3' yield, to be varied without corresponding changes in the thickness of the remaining portions of the layers or in the major film processing or manipulative characteristics of the film 4'. Conversely, the range of conditions for which the bulk film and tape stock display inelastic properties may be increased by the use of relatively thicker outer layers 2', 3' as shown in FIG. 1A without significant changes in the mechanical yield point or range of yield points at which converted tape products achieve their elastic properties.

FIG. 4 illustrates another diaper fastening tab construction embodying the invention, and which also includes the features and advantages of the teaching of U.S. Pat. No. 4,020,842 of common assignee, whose disclosure is adopted by reference. Here the outer layer that is deployed by the end user when the diaper is applied includes not only the film 4, release 5 and pressure-sensitive adhesive 6, but also the film 14, release 15 and pressure-sensitive adhesive 16. As shown, the adhesive layer 16 has a gap at the central segment of the fastener. The film 14 is preferably non-stretchy but, similarly to the construction shown in U.S. Pat. No. 4,020,842, is provided with a split S, which, in the present invention as shown in FIG. 4, also accommodates stretching of the film 4 at the central segment in the manner previously described in connection with the embodiments of FIGS. 2 and 3.

When the deployed end segment is stretched around an infant or adult to whom the diaper is being applied, the film 4 stretches and the layers 2 and 3 yield at the central segment in the manner previously described.

Upon initial fastening of the diaper, the adhesive layer 16 at the deployed end segment is applied to the diaper by the person fastening the diaper. The diaper can be reopened temporarily for inspection or adjustment by peeling the film 4 and adhesive layer 6 from the release 15 on film 14. Upon such reopening, the portions of the film 14 and adhesive 16 which are on the same side of the split S as the deployed end segment are "left behind" on the diaper, and provide a convenient "landing zone" for receiving the adhesive layer 6 and film 4 to accomplish subsequent reclosing of the diaper if such is desired.

Since layer 1 retains its elasticity at all times, when the fastener shown in FIG. 4 is reopened, the fastener recovers from its stretched state to substantially its original length. When the fastener is then refastened, it is easily again stretched around the infant or adult wearing the diaper to again maintain a comfortable fit of the fastened diaper.

The provision of elastic properties by stretching or tensioning film material is illustrated by the stress-strain curves for sequential test cycles shown in FIGS. 7 through 10 for different film constructions summarized in Table I below. The multiple layer film construction including elastic and inelastic layers with stretching of the latter beyond its yield point results in a distinct hybrid combination of plastic and elastomeric properties in an initial elongation.

TABLE I

| EXAMPLE | LAYER THICKNESS - MICRONS (MILS) | | |
| --- | --- | --- | --- |
| | MIDDLE-1 | OUTER-2 | OUTER-3 |
| 1 | 160 (6.4) | 9 (0.4) | 9 (0.4) |
| 2 | 151 (6.0) | 3 (0.1) | 8 (0.3) |
| 3 | 163 (6.5) | 8 (0.3) | 9 (0.4) |
| 4 | 201 (8.0) | 5 (0.2) | 5 (0.2) |

In each of the examples, the outer layers are polypropylene. In each of examples 1, 2 and 4, the middle layer is an 85:15 mixture of KRATON 1102 and low density polyethylene. In example 3, the middle layer is a 90:10 mixture of KRATON 1102 and low density polyethylene. In all examples, the indicated thicknesses are substantially uniform throughout the layer.

The test samples of the films of examples 1–4 were taken in the machine cross-direction so that the test sample length extends in the cross-direction and the test sample width extends in the machine direction. This is the same orientation used in the tape products manufactured from bulk film and tape stock as described above.

Each of the curves in FIGS. 7-10 indicates the tensile force experienced by a one-inch wide test sample of film elongated in its lengthwise direction at a constant rate of 12 inches/min. from a zero elongation starting point to 400% elongation, the test sample then being allowed to recover and return to its starting point at the same rate. This elongation and recovery test cycle is repeated and the tensile force experience of the film is continuously shown by the corresponding cycle curve.

Referring to FIG. 7, an initial elongation or first cycle stress-strain curve 1 for example 1 includes an initial portion 1A, a generally horizontal 1A' and a curved return portion 1B. The curve portions 1A and 1A' of curve 1 are believed to reflect the combined effect of the outer layers 2, 3 of the film and such portions of the curve approximately conform with a generalized stress-strain curve for plastic. Billmeyer, *Textbook of Polymer Science*, p. 127, Second Edition, 1971. Accordingly, the curve portion 1A is steeply sloped indicating a relatively high modulus of elasticity with little or no strain resulting and the film exhibits substantially inelastic properties as contemplated herein.

Upon extension of the film to the yield point or range of yield points of the layers 2 and 3 as generally indicated at "Y" in FIG. 7, the curve portion 1A' begins and extends to the 400% elongation point with continued stretching of the film. The forces indicated by curve portion 1A' are believed associated primarily with irreversible deformation of the outer layers 2 and 3 of the film.

The recovery and return of the film of example 1 to its starting point condition is indicated by the curve portion 1B which generally conforms with a stress-strain curve for a typical elastomer, Billmeyer, p. 195, supra. Accordingly, this portion 1B of the curve 1 is believed to be associated with the elastomeric middle layer 1 of the film of example 1.

The next elongation cycle of the film of example 1 is shown as curve 2 in FIG. 7. Curve 2 has a substantially less steep initial portion 2A, as compared with the curve portion 1A. Curve 2 does not include a horizontal portion corresponding with portion 1A' of curve 1 since the outer layers 2 and 3 of the film are ruptured or otherwise deformed in the initial cycle so as to no longer significantly contribute to the physical properties of the film. Curve 2 includes a return portion 2B which is similar to the curve portion 1B. Accordingly, curve 2 is believed to primarily result from the behavior of the elastomeric middle layer 1 of the film of example 1, and the film now displays its elastic properties.

Curves 3 and 4 in FIG. 7 indicate additional elongation and recovery cycles in which the physical properties of the film are believed to be substantially provided by the middle layer 1. The elastic properties of the film are maintained in subsequent elongation and recovery cycles.

Figure 8:
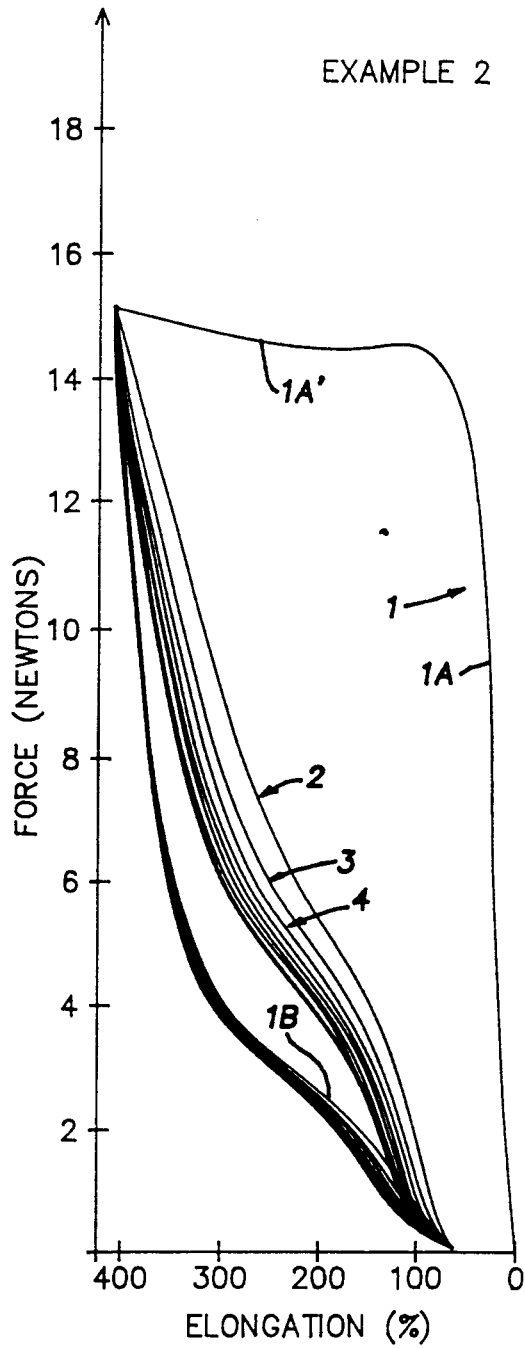
FIG. 8 is a reproduction of stress-strain curves for multiple sequential elongation and recovery cycles for the film of Example 2.
Figure 9:
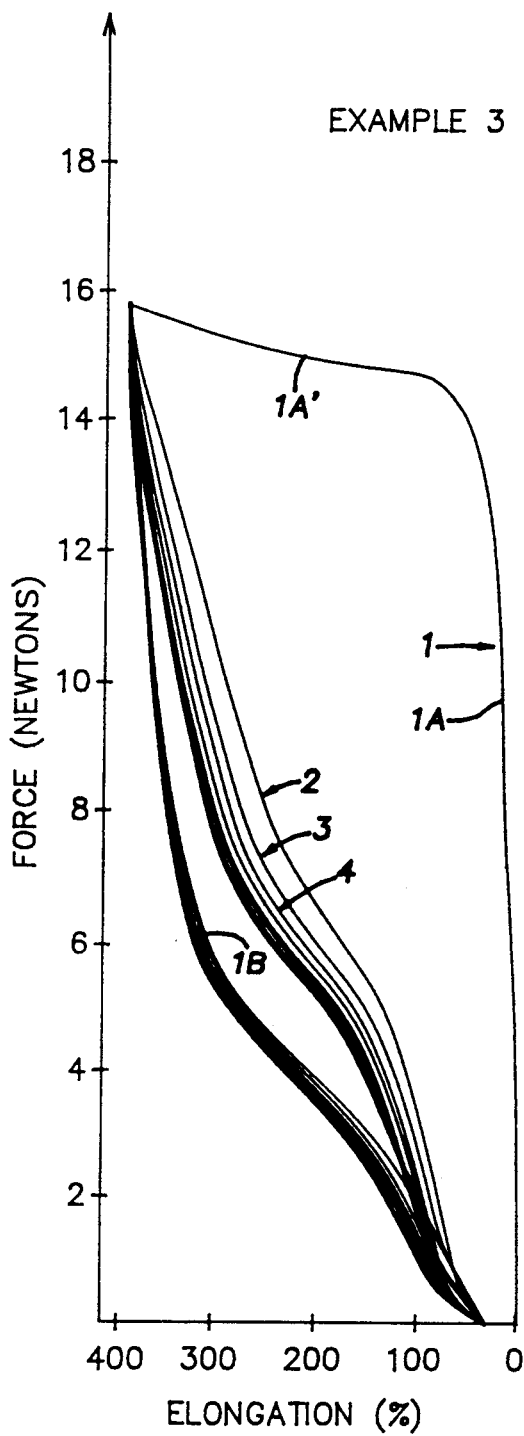
FIG. 9 is a reproduction of stress-strain curves for multiple sequential elongation and recovery cycles for the film of Example 3.
Figure 10:
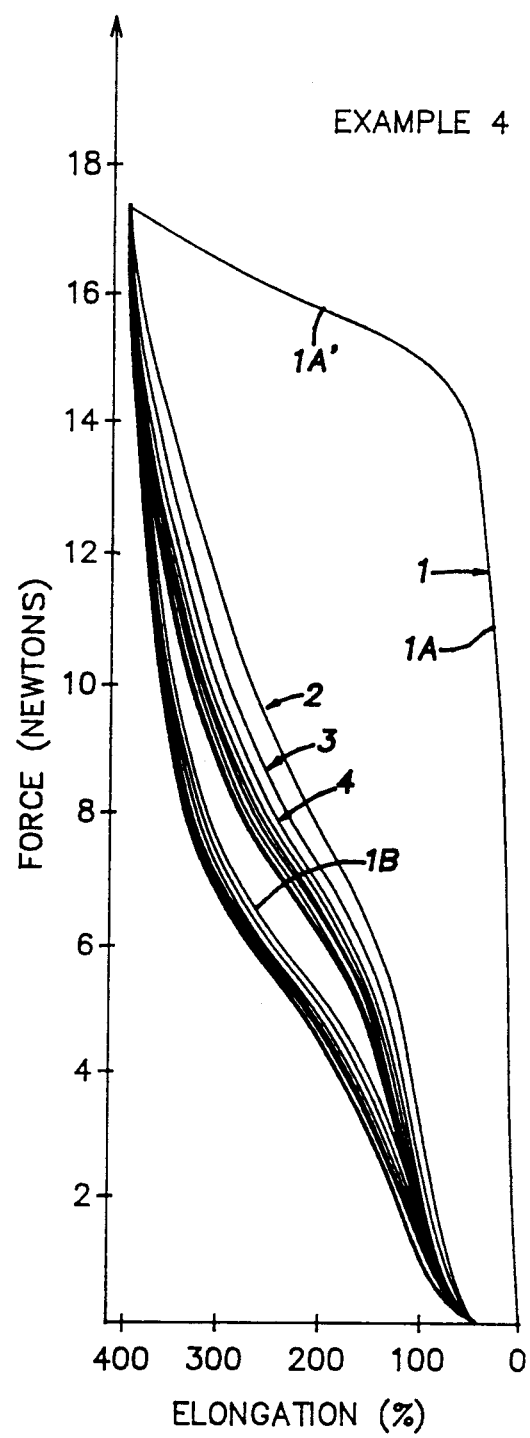
FIG. 10 is a reproduction of stress-strain curves for multiple sequential elongation and recovery cycles for the film of Example 4.

Referring to FIGS. 8, 9 and 10, stress-strain curves for sequential test cycles are shown for examples 2, 3 and 4 respectively. In each case, the curve for the initial test cycle is identified as curve 1 and the curves for the subsequent cycles are sequentially numbered. In each case, curve 1 indicates a stress-strain curve for a plastic material during elongation as shown by curve portions 1A and 1A'. Each of the examples also displays elastomeric stress-strain curves during elongation cycles subsequent to the initial cycle.

The concepts and teaching of the invention do not necessarily require quantification. However, it may be desirable, in some aspects of the invention, to specify desirable values. Thus, it is considered desirable according to the invention to provide film properties such that the force per unit width (F1-100) required to elongate the film to the 100% elongation point is at least 50% of the force per unit width (F1-400) required to elongate the film to 400% elongation point in an initial elongation, and, in a second elongation, the force per unit width (F2-100) required to elongate the film to 100% is substantially less than 50% of the force per unit width (F1-400) to initially elongate the film to 400% elongation. More preferably, the force per unit width (F1-50) to elongate the film to the 50% elongation point is at least 70% of the force (F1-400) required for 400% elongation in the initial elongation cycle, and in a second elongation, the force (F2-50) to elongate the film to 50% elongation is substantially less than 30% of the force (F1-400) to initially elongate the film 400%.

Referring to FIG. 7, a force (F1-400) of 17.1N is required for 400% elongation and a force (F1-50) of 16.0N is required for 50% elongation in the initial elongation of the film of example 1. Accordingly, the force (F1-50) for 50% elongation is 93.6% of the force (F1-400) for 400% elongation in example 1. In a subsequent elongation to the 50% elongation point, the required force (F2-50) is substantially less force than 30% of the force (F1-400) of the initial 400% elongation. The foregoing relationships are summarized below in Table II.

Examples 2, 3 and 4 are also summarized in Table II with respect to the F1-50/F1-400 percentage and the F2-50/F1-400 percentage. For each of the examples, the F1-50/F1-400 percentage is substantially higher than 70% and the F2-50/F1-400 percentage is substantially less than 30%.

TABLE II

| EXAMPLE | F1-400 (N) | F1-50 (N) | F1-50/ F1-400 (%) | F2-50 (N) | F2-50/ F1-400 (%) |
| --- | --- | --- | --- | --- | --- |
| 1 | 17.1 | 16.0 | 93.6 | <0.6 | <3.2 |
| 2 | 15.1 | 14.1 | 93.4 | <0.5 | <3.3 |
| 3 | 15.8 | 13.9 | 88.0 | <0.5 | <3.2 |
| 4 | 17.4 | 14.3 | 82.2 | <0.5 | <2.9 |

The foregoing elongation relationships exemplify preferred physical characteristics of films in accordance with the invention for use in diaper fastener constructions. Other relationships may be suitable for different film and tape applications. In all cases, the film properties may be varied by the use of particular layer materials, relative layer thicknesses and special film configurations such as those shown in FIG. 1A.

In further illustration of tape applications, the multiple layer film may be used also in prelaminated tape constructions such as the diaper tape closure shown in U.S. Pat. No. 4,726,971 and the stretchable variation thereof shown in European patent publication No. 247,855, published Dec. 2, 1987. The multiple layer film of the invention may be used in place of the tape backing in the diaper tab of the '971 patent to provide directly a stretchable tab construction or it may be substituted for the elastomeric layer in the diaper tab of the '855 publication.

The multiple layer film of this invention may be used in stretchable fastening devices and tapes which include an attachment or fastening layer such as, for example, a hook and loop fastener or other non-pressure-sensitive adhesive system instead of a pressure-sensitive adhesive fastening layer.

The film of the invention may be used in extendible diaper tabs as shown in U.S. Pat. Nos. 4,063,559 and 4,389,212. Such diaper tabs have extensible or stretchable portions which may be provided by use of the film disclosed herein.

The invention is not limited to all the details described above. Obviously, stretchable films and fastening devices and systems may be provided which change, eliminate or add specific details without departing from the invention. For example, in some instances it may be practical to use a film similar to the film 4 but consisting of the layer 1 and only one of the layers 2 and 3. In other words, one of the layers 2 and 3 may be omitted, in which case the other will generally be given a greater thickness than would be given when both are used. If one of layers 2 and 3 is omitted, it may be preferable to omit layer 2, so that layer 3 may continue to be utilized not only as an inelastic layer but also as a barrier to prevent unwanted migration of solvents, compounds or agents between the adhesive layer 6 and the elastic layer 1. Without such a barrier, such migration might occur, particularly if it happens that there is an extended period of time between the day the fastening tape stock is manufactured and the day a diaper is fastened using a fastener made from that stock.

A further variant comprises embossing or microembossing the film 4. Such processing is not believed to adversely affect the properties of the films nor the tape constructions.

Another variant would be to replace the fingerlift arrangements provided by the staggered terminations of the layers at the left ends of the constructions as seen in FIGS. 2, 3 and 4 by plastic strips inserted between layers at such ends in the manner disclosed for example in the aforesaid U.S. Pat. No. 4,726,971 and European patent publication 247,855.

What is claimed is:

1. A pressure-sensitive stretchable fastening tape suitable for disposable diapers or other articles which are provided with a fastening tape, said tape having length, width and thickness directions, characterized in that said tape comprises a film and a pressure-sensitive adhesive layer associated with said film at the terminal segments thereof in its length direction to provide a central segment which is free of adhesive, said film comprising at least two layers, at least a first one of the layers being a substantially continous layer free of a perforated breakable joint and dimensionally stable up to a yield point or range where said layer yields under given manual stretching tensions while at least a second of the layers remains substantially completely elastic under the same tensions, the film prior to manual tensioning to said given tensions being at least partially inelastic, said film upon manual stretching to said given tensions becoming substantially completely elastic, said first layer having a central segment portion of reduced thickness aligned with said central segment of said adhesive layer.

2. A pressure-sensitive stretchable fastening tape suitable for disposable diapers or other articles which are provided with a fastening tape, characterized in that said tape comprises a film and a pressure-sensitive adhesive layer associated with said film at least at the terminal segments thereof, said film comprising at least two layers, at least a first one of the layers being a substantially continuous layer free of a perforated breakable joint and dimensionally stable up to a yield point or range where said layer yields under given manual stretching tensions while at least a second of the layers remains substantially completely elastic under the same tensions, the film prior to manual tensioning to said given tensions being at least partially inelastic, said film upon manual stretching to said given tensions becoming substantially completely elastic.

3. A pressure-sensitive stretchable fastening tape suitable for disposable diapers or other tab fastened articles comprising a pressure-sensitive adhesive layer associated with a film including at least two layers, at least a first one of the layers being a substantially continuous layer free of a perforated breakable joint and dimensionally stable up to a yield point or range where said layer yields under given manual stretching tensions while at least a second of the layers remains substantially completely elastic under the same tensions, the film prior to manual tensioning to said given tensions being at least partially inelastic, said film upon manual stretching to said given tensions becoming substantially completely elastic, and wherein said film is manufactured with machine and cross dimensions, and said yield point or range where said first layer yields is sufficiently high to permit the use of automatic film handling and coating machinery in the manufacturing and processing of said film having said machine and cross dimensions.

4. A tape as set forth in claims 1, 2 or 3, wherein said at least two layers are coextruded.

5. A tape according to claims 1, 2 or 3, wherein said film exhibits stress-strain characteristics of a plastic material in an initial elongation prior to manual stretching and stress-strain characteristics of an elastomeric material in elongations subsequent to manual stretching.

6. A tab fastener suitable for disposable diapers or other tab fastened articles, said tab fastener having length, width and thickness directions, comprising in the length direction first and second terminal seqments and a central segment therein between, and in its thickness direction an inner layer and an outer layer, said inner layer being permanently adhered to the article, and said outer layer being permanently adhered to the inner layer at said first terminal segment and releasably adhered at said second terminal segment, characterized in that the outer layer is itself layered at least to an extent to comprise a film including at least two layers, at least a first one of the layers being a substantially continuous layer free of a perforated breakable joint and dimensionally stable up to a yield point or range where said layer yields under given manual stretching tensions while at least a second of the layers remains substantially completely elastic under the same tensions, the film prior to manual tensioning to said given tensions being at least partially inelastic, said film upon manual stretching to said given tensions becoming substantially completely elastic.

7. A tab fastener as in claim 6 in which said outer layer is further layered to additionally comprise an additional substrate that, at said second terminal segment, separates from said inner layer when said outer layer is released from said inner layer as the second terminal segment is deployed to fasten a diaper, and thereafter is adapted to adhere to a portion of the diaper as the diaper is fastened by the person applying it, and to separate from said film and be "left behind" on said portion of the diaper as the diaper is reopened by lifting said film at said second terminal segment.

8. A tape as in claim 3, wherein in an initial elongation of the film by 400%, the force per unit width required to elongate the film to the 100% elongation point is at least 50% of the force per unit width required to elongate the film to the 400% elongation point, and in subsequent elongations of the film by 400%, the force per unit width required to elongate the film to the 100% elongation point is substantially less than 50% of the force per unit width required to elongate the film to the 400% elongation point.

9. A pressure-sensitive stretchable fastening tape suitable for disposable diapers or other articles which are provided with a fastening tape, said tape having length, width and thickness directions, characterized in that said tape comprises a film and a pressure-sensitive adhesive layer associated with said film at the terminal segments thereof in its length direction to provide a central segment which is free of adhesive, said first layer having a central segment portion of reduced thickness aligned with said central segment of said adhesive layer, said film consisting of three layers, characterized in that the outer layers are inelastic, substantially continuous and free of a perforated breakable joint and the middle layer is elastic and the film becomes substantially completely elastic, at least at one of its lengthwise portions, by manual stretching to overcome the dimensional stability of said outer layers.

10. A tape according to claim 9, wherein the middle layer has a thickness of 5-500 microns and comprises an elastomer and the outer layers have a thickness of 5-200 microns and comprise a material selected from the group consisting of plastics, paper and non-woven fiber web.

11. A pressure-sensitive stretchable fastening tape suitable for disposable diapers or other articles which are provided with a fastening tape, characterized in that said tape comprises a film and a pressure-sensitive adhesive layer associated with said film at least at the terminal segments thereof, said film consisting of three layers, characterized in that the outer layers are inelastic, substantially continuous and free of a perforated breakable joint and the middle layer is elastic and the film becomes substantially completely elastic, at least at one of its lengthwise portions, by manual stretching to overcome the dimensional stability of said outer layers.

12. A stretchable fastening tape suitable for disposable diapers or other articles which are provided with a fastening tape, said fastening tape having length, width and thickness directions, characterized in that said fastening tape comprises a film and a fastening layer associated with said film at least at the terminal segments thereof, said film consisting of three layers, characterized in that the outer layers are inelastic, substantially continuous and free of a perforated breakable joint and the middle layer is elastic and the film becomes substantially completely elastic, at least at one of its lengthwise portions, by manual stretching to overcome the dimensional stability of said outer layers.

13. A stretchable fastening tape suitable for disposable diapers or other articles which are provided with a fastening tape, said fastening tape having length, width and thickness directions, characterized in that said fastening tape comprises a film and a fastening layer associated with said film at least at the terminal segments thereof, said film comprising at least two layers, at least a first one of the layers being a substantially continuous layer free of a perforated breakable joint and dimensionally stable up to a yield point or range where said layer yields under given manual stretching tensions while at least a second of the layers remains substantially completely elastic under the same tensions, the film prior to manual tensioning to said given tensions being at least partially inelastic, said film upon manual stretching to said given tensions becoming substantially completely elastic.

* * * * *

UNITED STATES PATENT AND TRADEMARK OFFICE
CERTIFICATE OF CORRECTION

PATENT NO. : 5,057,097

DATED : October 15, 1991

INVENTOR(S) : Marc Gesp

It is certified that error appears in the above-identified patent and that said Letters Patent is hereby corrected as shown below:

```
Column 4, line 2, after "Accordingly," insert --reinforcing
process liners are not required.  The--.
```

Signed and Sealed this

Thirteenth Day of April, 1993

Attest:

STEPHEN G. KUNIN

Attesting Officer

Acting Commissioner of Patents and Trademarks